US00PP15180P2

(12) United States Plant Patent
Bradford

(10) Patent No.: US PP15,180 P2
(45) Date of Patent: Sep. 28, 2004

(54) CHERRY TREE NAMED 'GLENARE'

(50) Latin Name: *Prunus avium*
Varietal Denomination: Glenare

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 33 days.

(21) Appl. No.: 10/602,667

(22) Filed: Jun. 25, 2003

(51) Int. Cl.[7] ..... A01H 5/00
(52) U.S. Cl. ..... Plt./181
(58) Field of Search ..... Plt./181

(56) References Cited

U.S. PATENT DOCUMENTS

PP6,407 P 11/1988 Bradford ..... Plt./181
PP12,859 P2 8/2002 Bradford ..... Plt./181

*Primary Examiner*—Anne Marie Grunberg

(57) ABSTRACT

The present invention relates to a cherry tree, *Prunus avium*, and more particularly to a new and distinct variety broadly characterized by a large size, vigorous, hardy, self-sterile, productive and regular bearing tree. The fruit matures under the ecological conditions described in the latter part of May, with first picking on May 21, 2003. The fruit is uniformly medium to large in size, very sweet in flavor, oblate in shape, clingstone in type, firm in texture, red in flesh color, and dark red in skin color.

1 Drawing Sheet

Botanical classification: *Prunus avium.*

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of cherry tree, which has been denominated varietally as 'Glenare'. During the spring of 1990 I gathered fruit from several 'Tulare' (U.S. Plant Pat. No. 6,407) cherry trees located in my experimental orchard at Bradford Farms near Le Grand, Calif. in Merced County (San Joaquin Valley). The seeds from this fruit were removed, cracked, stratified, germinated, and grown as seedlings on their own root in my greenhouse, and upon reaching dormancy transplanted to a cultivated area of my experimental orchard described above. During the fruit evaluation season of 1995 I selected several cherry trees that exhibited desirable qualities. The present variety was selected as a single tree from the above group. Subsequent to origination of the present variety of cherry tree, I asexually reproduced it by budding and grafting in the experimental orchard described above, and such reproduction of plant and fruit characteristics were true to the original plant in all respects. The reproduction of the variety included the use of 'Colt' (unpatented) rootstock upon which the present variety was compatible and true to type.

The present variety is most similar to the 'Tulare' (U.S. Plant Pat. No. 6,407) cherry by blooming at the same time and by producing cherries that are medium to large in size, firm in texture, dark red in skin color, red in flesh color, and sweet in flavor, but is distinguished therefrom and an improvement thereon by producing cherries that are somewhat oblate in shape rather than heart shaped and by being a pollinator for both the 'Glenred' (U.S. Plant Pat. No. 12,859) and the 'Tulare'.

SUMMARY OF VARIETY

In summary, the present variety is characterized by a large size, vigorous, hardy, self-sterile, productive and regular bearing tree. The fruit matures under the ecological conditions described in the latter part of May, with first picking on May 21, 2003. The fruit is uniformly medium to large in size, very sweet in flavor, oblate in shape, clingstone in type, firm in texture, red in flesh color, and dark red over the entire surface in skin color.

DRAWING

The accompanying photograph displays four fruits with the stems attached, several whole fruits detached from the stems to exhibit the skin color and form, two fruits sectioned along different planes to reveal the flesh and fibers, and several leaves, all typical of the subject variety.

POMOLOGICAL CHARACTERISTICS

Referring now more specifically to the pomological characteristics of this new and distinct variety of cherry tree, the following has been observed under the ecological conditions prevailing near Le Grand, Merced County (San Joaquin Valley), Calif., at the state of firm ripe on May 25, 2003, on the original tree during the twelfth growing season. All major color code designations are by reference to the Inter-Society Color Council, National Bureau of Standards. Common color names are also used occasionally.

Tree

Size: Large, reaching a height of 18' [5.49 m.] and a spread of 13' [3.96 m.] after twelve growing seasons on its own root.

Vigor: Vigorous, responding typically to irrigation and fertilization. The plant should be grown on a standard commercial rootstock for production purposes.

Growth: Upright.

Form: A natural tendency to generate a central leader system if unpruned, but a vase shape may be obtained by pruning.

Branch angle range: 40 to 60 degrees.

Hardiness: Hardy with respect to central California winters.

Heat tolerance: Observed to perform adequately in typical central California climatic conditions, which typically include extended periods of heat.

Drough tolerance: Variety is developed for commercial orchards and requires regular irrigation.
Production: Productive.
Fertility: Self-sterile, must be cross pollinated by another early blooming cherry variety, such as 'Tulare' or 'Sequoia'.
Bearing: Regular bearer with no alternate bearing yet observed.
Trunk:
*Size.*—Medium, with a maximum diameter of 7½" [191 mm.] after the twelfth growing season.
*Texture.*—Shaggy.
*Bark color.*—Grayish brown [61. gy.Br].
*Lenticels.*—Approximate number per square inch: 6. Color: Moderate brown [58. m.Br]. Typical size: ¼" to ⅝" [6.4–15.9 mm.].
Branches:
*Main scaffold diameter.*—3¾" [95 mm.] measured 12" above the crotch.
*Limb diameter.*—1⅝" [41 mm.] measured 12" above the first fork.
*Texture.*—Smooth on 1st year wood, increasing roughness with age.
*Color.*—1st year wood topside: Grayish red [19. gy.R]. 1st year wood underside: Brilliant yellow green [116. brill.YG]. Older wood: Dark grayish brown [62. d.gy.Br].
*Lenticels.*—Approximate number per square inch: 12. Color: Moderate brown [58. m.Br]. Typical size: ⅛" to ⅜" [3.2–9.5 mm.].
Leaves:
*Size.*—Large. Average length: 5" [127 mm.]. Average width: 2 1/16" [52.4 mm.].
*Arrangement.*—Alternate.
*Thickness.*—Medium.
*Form.*—Elliptical.
*Apex.*—Acuminate.
*Base.*—Acute to rounded.
*Surface.*—Smooth.
*Color.*—Dorsal surface: Moderate olive green [125. m. OlG] to dark yellowish green [137. d.yG]. Ventral surface: Moderate yellow green [120. m.YG].
*Margin.*—Finely serrate.
*Venation.*—Pinnately net veined.
*Vein color.*—Light yellow green [119. l.YG].
*Petiole.*—Average length: 1⅜" [34.9 mm.]. Average thickness: 1 1/16" [27.0 mm.]. Color: Very dark purplish red [260. v.d.pR] topside blending to light yellow green [119. l.YG] underside.
*Stipules.*—Number: 2 long and up to 6 shorter per leaf. Average length: ½" [12.7 mm.]. Color: Pale yellow green [121. p.YG] becoming light reddish brown [42. l.rBr] when old and dry.
*Glands.*—Number: 2 per leaf. Position: On petiole. Size: Large. Form: Oval to reniform. Color: Dark red [16. d.R] edges and Grayish reddish orange [39. gy.rO] centers.
*Leaf buds.*—Pointed, conic.
Flower buds:
*Hardiness.*—Hardy, with respect to central California winters.
*Diameter.*—Typically 5/16" [7.9 mm.] right before bloom.
*Length.*—Typically ⅝" [15.9 mm.] right before bloom.
*Form.*—Free.
*Surface.*—Smooth.
*Color.*—White [263. white].

Flowers: Perfect, complete, perigynous, usually a single pistil, typically twenty or more stamens, five sepals and petal locations alternately positioned.
*Average flower diameter.*—1 3/16 [30.2 mm.].
*Number of petals.*—Usually five.
*Petal shape.*—Circular to oval.
*Petal margin.*—Somewhat wavy.
*Average petal diameter.*—9/16" [14.3 mm.].
*Average petal length.*—9/16" [14.3 mm.].
*Petal apex.*—Rounded.
*Petal base.*—Rounded to slightly cuneate.
*Petal color.*—White [263. white].
*Anther color.*—Light yellow [86. l.Y].
*Stigma color.*—Light yellow green [119. l.YG].
*Sepal color.*—Grayish purplish red [262. gy.pR].
*Sepal length.*—¼" [6 mm.].
*Sepal width.*—5/32" [4 mm.].
*Average pistil length.*—½" [12.7 mm.].
*Average stamen length.*—9/16" [14.3 mm.].
*Fragrance.*—Moderate.
*Blooming period.*—Early compared with other varieties.
*Onset of bloom.*—Five percent on Mar. 17, 2003, with 'Tulare'.
*Date of full bloom.*—Mar. 25, 2003.
*Duration of bloom.*—Five to ten days, dependent on ambient temperature.
*Number per cluster.*—Usually 2 to 5.

FRUIT

Maturity when described: Firm ripe, May 25, 2003.
Date of first picking: May 21, 2003.
Date of last picking: May 29, 2003.
Size: Uniform, medium to large.
*Average diameter axially.*—15/16" [23.8 mm.].
*Average cheek diameter.*—1 1/16" [27.0 mm.].
*Average diameter across suture plane.*—15/16" [23.8 mm.].
*Typical weight.*—0.32 ounces [9.2 grams].
Form: Uniform, symmetrical, compressed axially and around suture.
*Cheek plane form.*—Oblate.
*Suture plane form.*—Oval.
*Axial view form.*—Elliptical.
Source: An inconspicous Blackish red [21. blackish R] line located from stem cavity to apex.
Ventral surface: Rounded.
Lips: Equal.
Stem cavity: Flaring, circular, suture showing on one side.
*Depth.*—3/16" [4.8 mm].
*Breadth.*—½" [12.7 mm.].
Base: Rounded to cordate.
Apex: Rounded.
Pistil point: An inconspicuous Yellowish gray [93. yGy] dot depressed within the suture.
Stem: Medium.
*Average length.*—1½" [38.1 mm.].
*Average width.*—1/16" [1.6 mm.].
*Color.*—Brilliant yellow green [116. brill.YG] with some Grayish red [19. gy.R] tinting from sunlight.
*Attachment.*—Strong.
Skin:
*Thickness.*—Medium.
*Surface.*—Smooth.
*Tenacity.*—Tenacious to flesh.

*Astringency.*—Slightly astringent.
*Tendency to crack.*—Slight, none observed in wet season.
*Color.*—Very dark red [17. v.d.R] to dark red [16. d.R] over the entire surface.

Flesh:
*Color.*—Deep red [13. deep R] toward stone to Pale yellowish pink [31. p.yPk] with Pale yellow [89. p.Y].
*Surface of pit cavity.*—Very deep red [14. v.deepR] fibers breaking when twisted from the stone.
*Amygdalin.*—Moderate.
*Juice.*—Abundant, rich.
*Juice color.*—Moderate red [15. m.R].
*Texture.*—Firm, crisp.
*Fibers.*—Abundant.
*Ripens.*—Earliest at apex and shoulder.
*Flavor.*—Delicious blend of acid and sugar, 22 brix.
*Aroma.*—Slight.
*Eating quality.*—Very good.

STONE

Type: Clingstone.
Form: Obovoid.
External color: Light yellowish brown [76. l.yBr].
Pit wall color when cracked: Pale orange yellow [73. p.OY].
Internal cavity color: Light yellowish brown [76. l.YBr].
Average width: 3/8" [9.5 mm.].
Average length: 7/16" [11.1 mm.].
Average breadth: 5/16" [7.9 mm.].
Hilum: Narrow to oval.
Base: Rounded.
Apex: Rounded.
Sides: Equal.
Surface: Smooth.
Ridges: Two thin ridges along the ventral edge.
Average pit wall thickness: 1/16" [1.6 mm.].
Tendency to split: None observed.

Kernel:
*Form.*—Oval.
*Skin color.*—Pale yellow [89. p.Y].
*Pellicle color.*—Grayish yellow [90. gy.Y].
*Vein color.*—Light yellowish brown [76. l.yBr].
*Taste.*—Bitter.
*Viable.*—Yes.
*Average width.*—1/4" [6.4 mm.].
*Average length.*—3/8" [9.5 mm.].
*Amygdalin.*—Abundant.

USE

Market: Fresh market and long distance shipping.
Keeping quality: Good. Fruit quality observed to remain in good condition after 14 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of cherry tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of cherry tree, substantially as illustrated and decribed, that is most similar to the 'Tulare' (U.S. Plant Pat. No. 6,407) cherry by blooming at the same time and by producing cherries that are medium to large in size, firm in texture, dark red in skin color, red in flesh color, and sweet in flavor, but is distinguished therefrom and an improvement thereon by producing cherries that are somewhat oblate in shape rather than heart shaped and by being a pollinator for both the 'Glenred' (U.S. Plant Pat. No. 12,859) and the 'Tulare'.

* * * * *

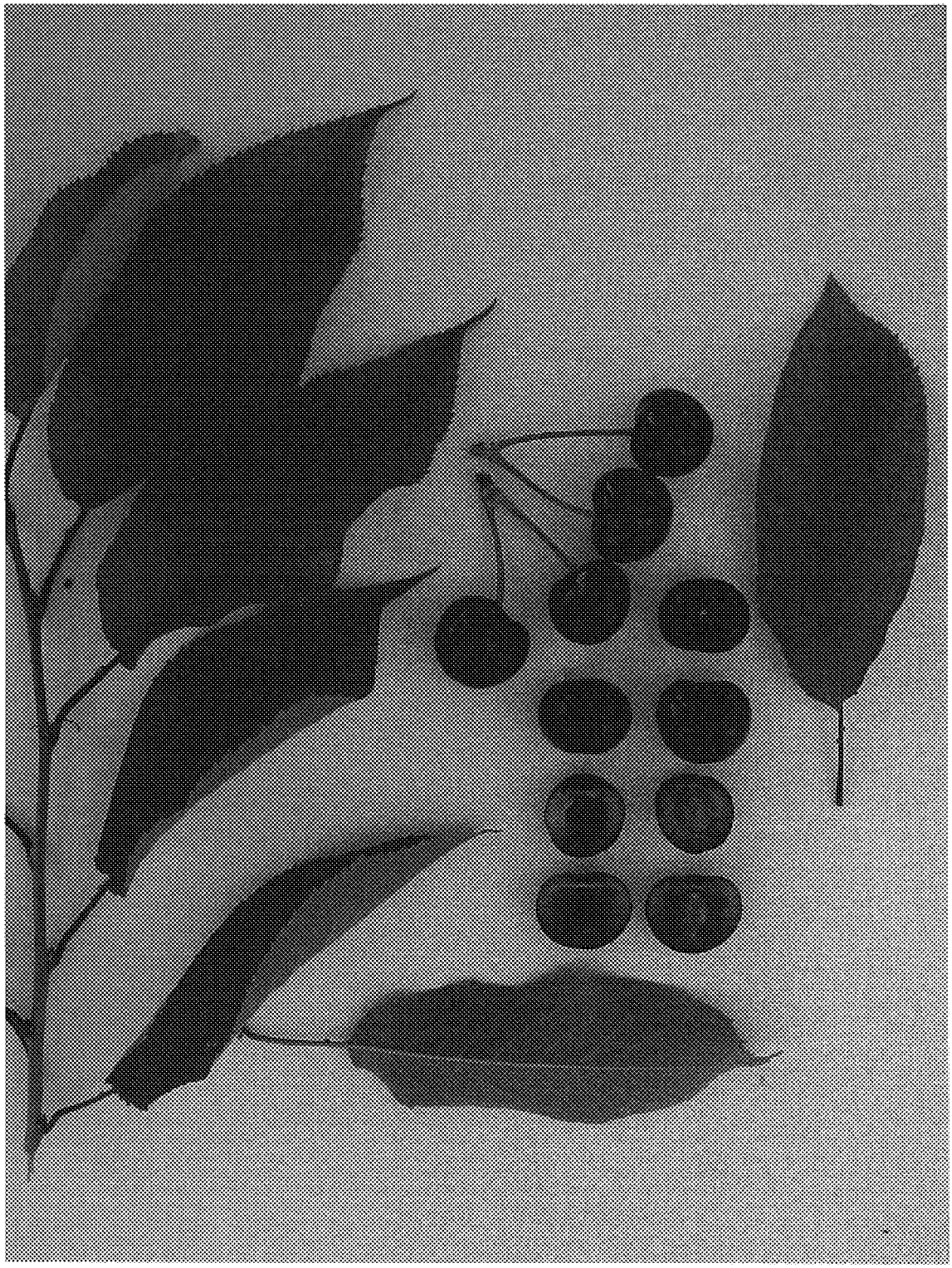

UNITED STATES PATENT AND TRADEMARK OFFICE

CERTIFICATE OF CORRECTION

PATENT NO. : PP 15,180 P2
APPLICATION NO. : 10/602667
DATED : September 28, 2004
INVENTOR(S) : Lowell Glen Bradford It is certified that error appears in the above-identified patent and that said Letters Patent is hereby corrected as shown below:

Column 3: Line 6: Replace " 'Sequoia' " with --'Glenred'--

Signed and Sealed this

Sixth Day of March, 2007

JON W. DUDAS
*Director of the United States Patent and Trademark Office*